(12) United States Patent
Onishi

(10) Patent No.: US 10,444,166 B2
(45) Date of Patent: Oct. 15, 2019

(54) RADIATION DETECTION DEVICE, RADIATION INSPECTION SYSTEM, AND METHOD FOR ADJUSTING RADIATION DETECTION DEVICE

(71) Applicant: HAMAMATSU PHOTONICS K.K., Hamamatsu-shi, Shizuoka (JP)

(72) Inventor: Tatsuya Onishi, Hamamatsu (JP)

(73) Assignee: HAMAMATSU PHOTONICS K.K., Hamamatsu-shi, Shizuoka (JP)

(*) Notice: Subject to any disclaimer, the term of this patent is extended or adjusted under 35 U.S.C. 154(b) by 0 days.

(21) Appl. No.: 16/062,726

(22) PCT Filed: Dec. 8, 2016

(86) PCT No.: PCT/JP2016/086586
§ 371 (c)(1),
(2) Date: Jun. 15, 2018

(87) PCT Pub. No.: WO2017/110508
PCT Pub. Date: Jun. 29, 2017

(65) Prior Publication Data
US 2019/0003990 A1    Jan. 3, 2019

(30) Foreign Application Priority Data

Dec. 21, 2015 (JP) ................................. 2015-248651

(51) Int. Cl.
*G01N 23/083* (2018.01)
*G01N 23/18* (2018.01)
(Continued)

(52) U.S. Cl.
CPC ......... *G01N 23/083* (2013.01); *G01N 23/087* (2013.01); *G01N 23/18* (2013.01);
(Continued)

(58) Field of Classification Search
CPC ..... G01N 23/083; G01N 23/087; G01N 23/18
See application file for complete search history.

(56) References Cited

U.S. PATENT DOCUMENTS 4,189,645 A    2/1980    Chaney et al.
5,986,257 A    11/1999   Harding
(Continued)

FOREIGN PATENT DOCUMENTS

EP    2352014 A1    8/2011
JP    S57-053677 A    3/1982
(Continued)

OTHER PUBLICATIONS

International Preliminary Report on Patentability dated Jul. 5, 2018 for PCT/JP2016/086586.

*Primary Examiner* — Hugh Maupin
(74) *Attorney, Agent, or Firm* — Drinker Biddle & Reath LLP

(57) ABSTRACT

An X-ray detection device is a device that detects X-rays having transmitted through a test subject, and comprises a filter that attenuates some of X-rays, a detector that detects the transmitted X-rays partially attenuated by the filter, a housing, and a holder that has one slit. The detector includes a line sensor, and a line sensor disposed in parallel and close to the line sensor. The holder holds the filter at a predetermined position so that the filter can cover a part of the slit, and the line sensor detects the X-rays attenuated by the filter.

15 Claims, 8 Drawing Sheets

(51) Int. Cl.
*G01T 1/20* (2006.01)
*G01T 7/00* (2006.01)
*G01N 23/087* (2018.01)

(52) U.S. Cl.
CPC .............. *G01T 1/20* (2013.01); *G01T 1/2018* (2013.01); *G01T 7/00* (2013.01)

(56) References Cited

U.S. PATENT DOCUMENTS

| | | | |
|---|---|---|---|
| 2002/0191738 A1* | 12/2002 | Mazess | G01N 23/06 378/57 |
| 2007/0064868 A1 | 3/2007 | Kostka et al. | |
| 2012/0236987 A1 | 9/2012 | Ruimi et al. | |
| 2013/0075618 A1* | 3/2013 | Takihi | G01N 23/04 250/366 |
| 2017/0184514 A1* | 6/2017 | Suyama | G01N 23/04 |

FOREIGN PATENT DOCUMENTS

| | | |
|---|---|---|
| JP | S64-086087 A | 3/1989 |
| JP | H4-132991 A | 5/1992 |
| JP | 2000-131446 A | 5/2000 |
| JP | 2002-168803 A | 6/2002 |
| JP | 2005-321334 A | 11/2005 |
| JP | 2010-117170 A | 5/2010 |
| JP | 2010-122103 A | 6/2010 |
| JP | 2013-156172 A | 8/2013 |
| JP | 2015-167722 A | 9/2015 |

\* cited by examiner (a)

(b)

RADIATION DETECTION DEVICE, RADIATION INSPECTION SYSTEM, AND METHOD FOR ADJUSTING RADIATION DETECTION DEVICE

TECHNICAL FIELD

The present invention relates to a radiation detection device, a radiation inspection system, and a method for adjusting a radiation detection device.

BACKGROUND ART

It is widely practiced that a test subject, such as a food or a pharmaceutical product, is irradiated with X-rays, and inspected for presence or absence of a foreign matter in the subject from a transmitted X-ray image thereof. An X-ray detection device that includes a line sensor for detecting a transmission image by X-rays emitted from an X-ray source toward the subject is used for the inspection. The X-ray detection device adopts, for example, a configuration where two line sensors are arranged in parallel in such a way as to detect X-rays in different energy ranges, in a case where foreign matters to be detected are different (for example, whether the foreign matter is a piece of bone or metal included in meat). In a case of obtaining a subtraction image from X-ray images through the two line sensors, it is preferable to reduce the interval between the line sensors in order to obtain a clearer image. Accordingly, for example, it has been proposed to form two line sensors in parallel on a common sensor substrate and reduce the interval (dead-zone region) between the two line sensors (for example, see FIG. 3 in Patent Literature 1).

CITATION LIST

Patent Literature

Patent Literature 1: Japanese Unexamined Patent Publication No. 2010-117170
Patent Literature 2: Japanese Unexamined Patent Publication No. 2002-168803

SUMMARY OF INVENTION

Technical Problem

Incidentally, in the X-ray detection device capable of detecting different foreign matters, it is preferable that the device can flexibly change the detection sensitivity to detect X-rays in various energy ranges in conformity with usage in consideration of the S/N ratio. In this case, it is required to change the scintillator or add a filter for adjustment. However, it is difficult to replace the scintillator every time adjustment is performed. On the other hand, the configuration of changing the filter is proposed in Patent Literature 2, for example. However, according to the configuration of Patent Literature 2, the sensors are relatively large and are independent of each other. It is difficult to apply, as it is, to the configuration where the two line sensors are disposed close to each other as in Patent Literature 1.

The present invention has been made in view of such problems, and has an object to provide a radiation detection device including line sensors disposed close to each other, the device being capable of easily changing the detection sensitivity to any of various energy bands, a radiation inspection system that includes the radiation detection device, and a method for adjusting the radiation detection device.

Solution to Problem

A radiation detection device according to one aspect of the present invention is a radiation detection device for detecting radiation which is irradiated to a test subject from a radiation source and is transmitted through the test subject. The radiation detection device comprises a filter that attenuates a part of the incident radiation; a detector that detects the radiation with a part thereof having been attenuated by the filter; a housing that place the detector therein; and a holder disposed on a principal surface of the housing to hold the filter, the holder including a first slit allowing the incident radiation to pass. In the radiation detection device, the detector comprises a first line sensor including pixels having a first pixel width, the pixels being one-dimensionally arranged; and a second line sensor including pixels having a second pixel width, the pixels being one-dimensionally arranged, the second line sensor being disposed in parallel to the first line sensor with an interval narrower than the first and second pixel widths, the holder holds the filter at a predetermined position so that the filter can cover at least a part of the first slit, and the second line sensor detects the radiation attenuated by the filter.

The radiation detection device is provided with, as the detector, the first and second line sensors disposed close to each other. The holder holds the filter at the predetermined position so that a part of the first slit included in the holder can be covered with the filter, thereby allowing the second line sensor to detect the radiation attenuated by the filter. As described above, the holder capable of positioning the filter is separately provided, which can easily change the type of the filter that attenuates the radiation. As a result, according to the aspect of the present invention, in the radiation detection device where the line sensors are disposed close to each other, the detection sensitivities can be easily changed to various energy bands.

In the radiation detection device described above, the holder may comprise a positioning section that positions the filter so that the first slit can be partially covered with the filter. In this case, as the positioning section is included in the holder, even with replacement of various filters having different materials and thicknesses, the replaced filter is securely positioned at the predetermined site, which can easily maintain the state where the first line sensor detects the radiation having not been attenuated by the filter and the second line sensor detects the radiation having been attenuated by the filter. In this case, it is preferable that the positioning section have a configuration of fixing the filter at the opposite ends in the longitudinal direction. Such adoption of the configuration of fixation at the opposite ends can suppress adverse effects and the like of the positioning section on detection of radiation at a central region.

In the radiation detection device described above, the distance between the filter and the second line sensor may range from 10 to 30 mm, inclusive. In this case, the adverse effects of the scattered radiation of emitted radiation can be reduced, and the transmitted radiation can be detected by each of the line sensors at a high sensitivity.

In the radiation detection device described above, the detector may further comprise a first scintillator disposed above the first line sensor, and a second scintillator disposed above the second line sensor. In this case, for example, scintillators having different performances can be adopted as the first and second scintillators, and the same sensors can be adopted as the first and second line sensors. On the other hand, the first and second line sensors may be a direct conversion type radiation detector. In this case, there is no need to provide the scintillators separately, thereby allowing the number of components to be reduced.

In the radiation detection device described above, the housing may include a second slit corresponding to the first slit of the holder. In this case, the transmitted radiation to be detected by each line sensor passes through the first and second slits, and the adverse effects of the material of the housing on detection of the transmitted radiation by each line sensor can be reduced. Note that in this case, the radiation detection device described above may further comprise a light shield film that covers the second slit, and the light shield film may be disposed between the holder and the housing. In this case, foreign matters (powder, dust, etc.) can be prevented from entering the inside of the housing through the second slit.

In the radiation detection device described above, the first line sensor may detect the radiation having not been attenuated by the filter. The first line sensor may detect the radiation having been attenuated by the filter.

The present invention relates to a radiation inspection system as another aspect, this radiation inspection system comprises a radiation source irradiating the test subject with radiation; any of the radiation detection devices described above; and a conveyer machine that conveys the test subject in a direction intersecting with a radiation direction of the radiation by the radiation source. As with the above description, this inspection system can easily change the type of the filter that attenuates the radiation. Consequently, the detection sensitivities in the radiation detection device, where the line sensors are disposed close to each other, can be easily changed to various energy bands, and various types of test subjects can be inspected.

The present invention relates to a method for adjusting any of the radiation detection devices described above as still another aspect. This adjustment method comprises preparing a plurality of filters having different attenuation functions, as the filter; sequentially holding the plurality of filters at a predetermined position of the holder, and detecting the radiation for each filter; and selecting an optimal filter among the filters according to results of the detected radiation. In this case, the optimal filter can be easily selected from among the filters having different attenuation functions. Consequently, the method for adjusting the radiation detection device can be easily performed, and the detection sensitivity in the radiation detection device can be easily changed to various energy bands. Note that according to the present invention, in the radiation detection device adjusted by the adjustment method, the radiation detection device may be manufactured by further comprising holding and fixing the optimal filter selected by the selecting at the predetermined position of the holder. Such a manufacturing method can easily manufacture the radiation detection device that can easily change the detection sensitivity to various energy bands.

Advantageous Effects of Invention

According to the present invention, in the radiation detection device where the line sensors are disposed close to each other, the detection sensitivities can be easily changed to various energy bands.

DESCRIPTION OF EMBODIMENTS

Hereinafter, referring to the accompanying drawings, preferred embodiments of the present invention are described in detail. In the description, the same signs are used for the same elements or elements having the same functions, and redundant description is omitted.

Figure 1:
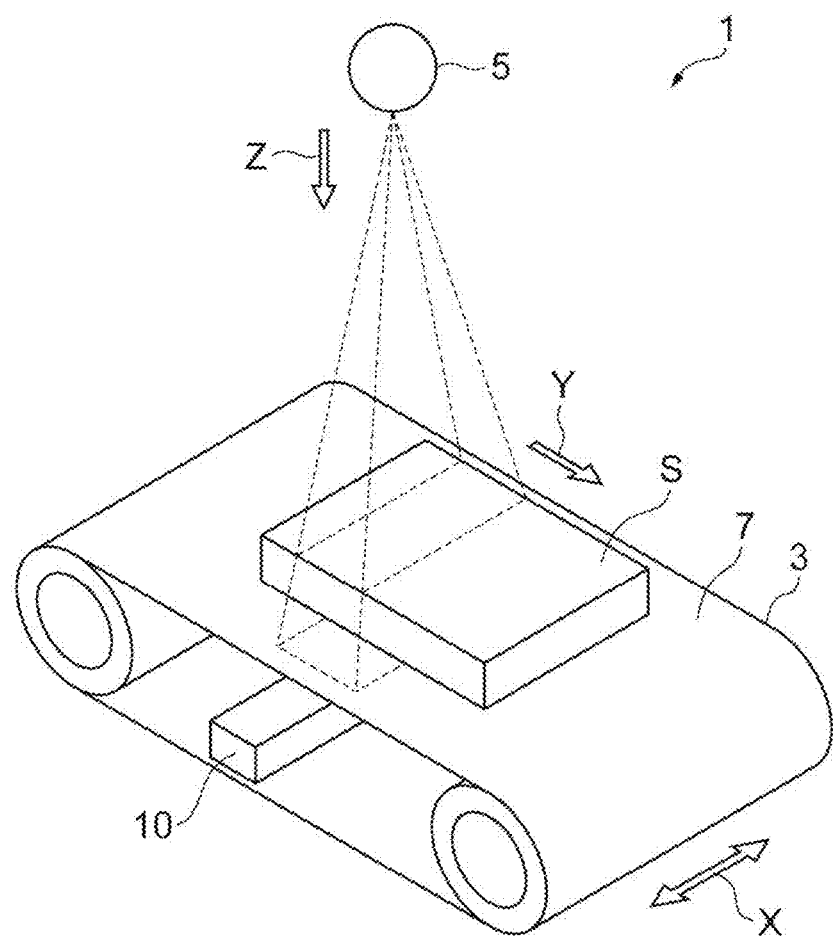
FIG. 1 is a perspective view schematically showing an X-ray inspection system according to this embodiment.
Figure 2:
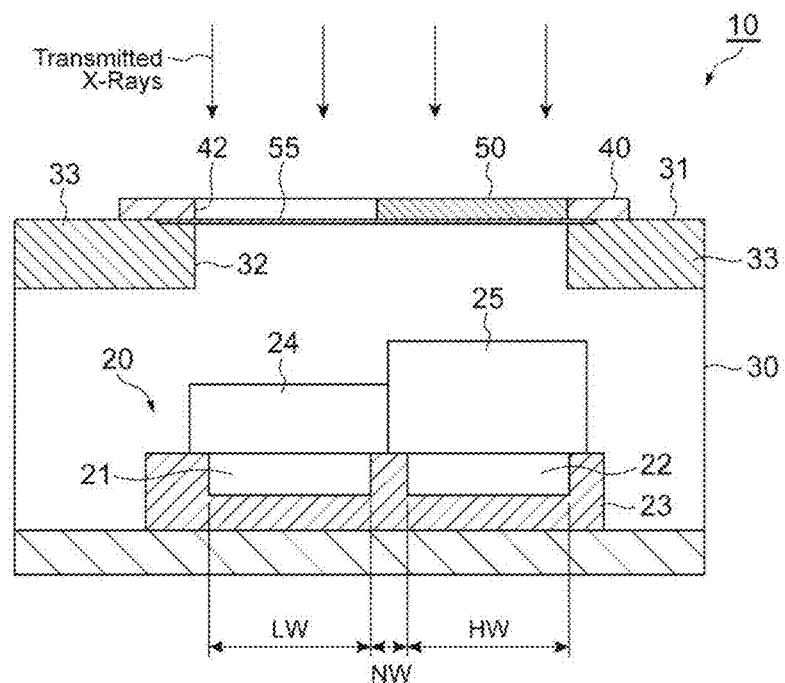
FIG. 2 is a sectional view schematically showing an X-ray detection device according to this embodiment.

FIG. 1 is a perspective view schematically showing an X-ray inspection system according to this embodiment. FIG. 2 is a sectional view schematically showing the X-ray detection device according to this embodiment. As shown in FIG. 1, an X-ray inspection system 1 (radiation inspection system) includes a belt conveyer 3 (conveyer machine), an X-ray irradiator 5 (radiation source), and an X-ray detection device 10 (radiation detection device). The X-ray inspection system 1 emits X-rays from the X-ray irradiator 5 in an irradiation direction Z to irradiate a test subject S, and detects transmitted X-rays having transmitted through the test subject S among the irradiation X-rays in a plurality of energy ranges. The X-ray testing system 1 performs a foreign matter inspection, a baggage inspection and the like using an image by the transmitted X-rays. The test subjects S by the X-ray inspection system 1 widely include, for example, foods, such as meat and retort foods, rubber products, such as tires, baggage to be baggage-inspected, resin products, metal products, such as wire, resource materials, such as minerals, waste to be segregated or resource-collected, electronic components and the like. Furthermore, there are various foreign matters to be detected in the test subject S. Accordingly, it is preferable that the X-ray inspection system 1 can flexibly change the detection sensitivity of each X-ray detection device 10 according to the physical property of the test subject S and the type of the foreign matter to be detected.

The belt conveyer 3 includes a belt unit 7 on which the test subject S is to be mounted. The belt conveyer 3 moves the belt unit 7 in a conveyance direction Y, thereby conveying the test subject S in the conveyance direction Y at a predetermined speed.

The X-ray irradiator 5 (radiation source) is a device that emits X-rays in the irradiation direction Z toward the test subject S and is, for example, an X-ray source. The X-ray irradiator 5 is, for example, a point light source, and performs irradiation of diffusing X-rays in a predetermined angle range in a detection direction X perpendicular to the irradiation direction Z and the conveyance direction Y. The X-ray irradiator 5 is disposed above the belt unit 7 apart by a predetermined distance from the belt unit 7 so that the X-ray irradiation direction Z can be oriented toward the belt unit 7, and the diffused X-rays can cover the substantially entire test subject S in the width direction (detection direction X). The X-ray irradiator 5 is configured such that in the longitudinal direction (conveyance direction Y) of the test subject S, a predetermined dividing range in the longitudinal direction is adopted as an irradiation range for one time, and the test subject S is conveyed by the belt conveyer 3 in the conveyance direction Y, thereby allowing the entire test subject S in the longitudinal direction to be irradiated with X-rays.

The X-ray detection device 10 (radiation detector) is a device that detects X-rays having been emitted from the X-ray irradiator 5 toward the test subject S and having transmitted through the test subject S, and is an X-ray detection camera, for example. The X-ray detection device 10 is disposed, for example, below the belt unit 7 to be disposed downstream of the test subject S in the radiation direction by the X-ray irradiator 5, for detecting the X-rays having transmitted through the test subject S. As shown in FIG. 2, which is a sectional view taken along the shorter side direction, such an X-ray detection device 10 includes a detector 20 that detects transmitted X-rays, a housing 30 that places the detector 20 therein, a holder 40 disposed on a principal surface 31 of the housing 30, and a filter 50 held by the holder 40. The filter 50 attenuates some of the X-rays having transmitted through the test subject S.

The detector 20 includes two line sensors 21 and 22, a substrate 23, and two scintillators 24 and 25, and detects the X-rays having been emitted from the X-ray irradiator 5 and having transmitted through the test subject S (the X-rays incident on the detection device) in different energy ranges. The line sensors 21 and 22 are formed adjacent to each other in the substrate 23, which is made of silicon. The line sensor 21 is a linear sensor where pixels having a pixel width LW are one-dimensionally arranged (the direction orthogonal to the sheet of FIG. 2; the X-direction in FIG. 1). The line sensor 22 is a linear sensor where pixels having a pixel width HW are one-dimensionally arranged. The line sensor 22 is disposed in such a way as to be arranged in parallel to the line sensor 21 at an interval NW that is narrower than the pixel widths LW and HW. The pixel widths LW and HW may be the same widths, for example, each about 0.6 mm, or may be different widths. The interval NW between the sensors may be about 0.2 mm, for example. A scintillator 24 for low energy is disposed on the line sensor 21. A scintillator 25 for high energy is disposed on the line sensor 22. In the example of FIG. 2, for example, the scintillators 24 and 25 are made of different materials or have different thicknesses, and can detect X-rays in different energy bands by means thereof.

The housing 30 includes one slit 32 (second slit) for allowing X-rays to pass therethrough, and shield members 33 made of lead or the like, on a side to be irradiated with X-rays. The housing 30 houses the detector 20 therein in such a way as to be disposed in a region that corresponds to the slit 32 and allows X-rays to be transmitted therethrough. A main body portion of the housing 30 other than the shield members 33 is made of aluminum, for example. Note that a light shield film 55 may be provided on the slit 32 and between this slit and the holder 40 to achieve a configuration of preventing particles and the like from entering the inside of the housing 30. The light shield film 55 may have a performance of attenuating some of the X-rays having transmitted through the test subject S.

The holder 40 is a planar holding member made of aluminum, for example, and has, at its center, one slit 42 (first slit) that substantially coincides with the length (the direction orthogonal to the sheet of FIG. 2) and the width (the lateral direction in FIG. 2) of the slit 32 of the housing 30. The slit 42 is only required to correspond to the slit 32, but is not necessarily required to coincide in both the length and width. For example, it may be configured such that the lengths substantially coincide with each other but the slit 42 has a larger width than the slit 32. The widths of the slits 32 and 42 are minute. For example, it is preferable that each slit be about 2 to 5 mm, that is, 5 mm or less.

The holder 40 causes positioning means to position the filter 50 and holds this filter so that the filter 50 can cover a part (for example, half a region in the width direction) of the single slit 42 to attenuate a part of (half) the transmitted X-rays. More specifically, the holder 40 positions and holds the filter 50 made of a linearly extending narrow width sheet so that an end (a left end in the diagram) in the width direction of the filter 50 can correspond to the region of the detector 20 between the line sensors 21 and 22 in the traveling direction of the transmitted X-rays. According to the positioning means, even after the holder 40 is replaced with a filter of a different type (thickness or material), the relative position with respect to the line sensors 21 and 22 is not changed. Accordingly, the filter 50 can be easily replaced. It is preferable that the filter 50 be held by the holder 40 to have distances with the line sensors 21 and 22 ranging 10 to 30 mm, inclusive.

Figure 3:
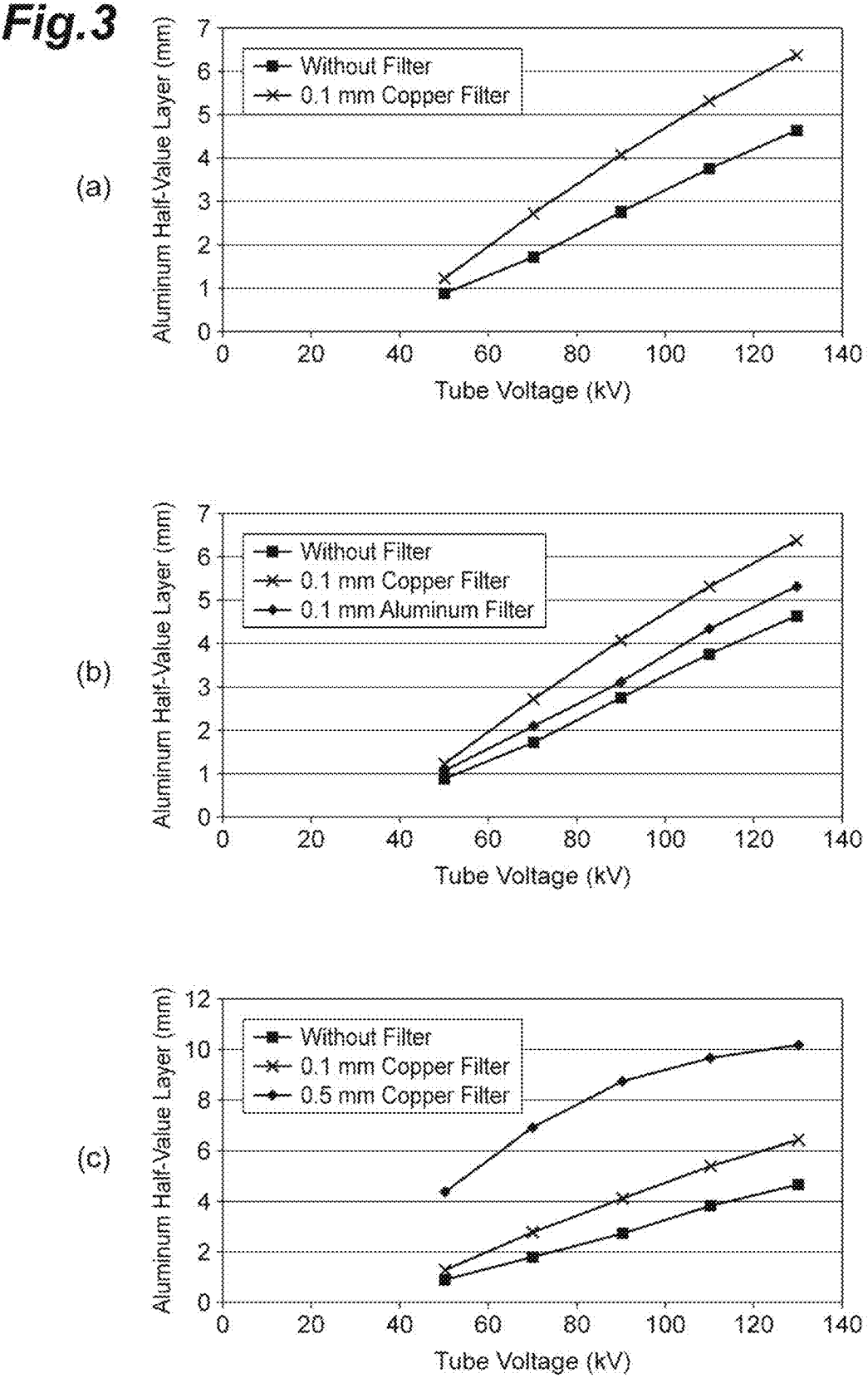
FIG. 3 is tables showing the relationship between the half-value layer and the tube voltage in cases of using copper and aluminum as filters, (a) shows comparison between a case with no filter and a case of using 0.1 mm thickness copper as a filter, (b) shows comparison between a case with no filter, a case of using 0.1 mm thickness copper as a filter, and a case of using 0.1 mm thickness aluminum as a filter, and (c) shows comparison between a case with no filter, a case of using 0.1 mm thickness copper as a filter, and a case of using 0.5 mm thickness copper as a filter.

The filter 50 held by the holder 40 as described above is a member that is formed of a material different from that of the test subject S to have a thin plate shape, and is made of, for example: a resin, such as polystyrene, polyethylene, polyurethane, polypropylene, Teflon®, ABS resin, AS resin, acrylic, polyamide, PET, GF-PET, PBT, polycarbonate, PPS, PTFE, PSF, or PI; carbon fiber material, such as amorphous carbon, or graphite; or metal, such as beryllium, aluminum, titanium, iron, zinc, molybdenum, tin, gold, silver, copper, platinum, lead, tantalum, gadolinium, holmium, or ytterbium. The material of the filter 50 is appropriately selected from among the aforementioned materials and the like according to a desired attenuation, i.e., the energy difference of the X-rays received by both the line sensors, and the S/N ratio. For example, it is preferable that the material be selected from copper and aluminum. Copper and aluminum have an X-ray shielding performance and are easily processed. Consequently, adjustment of the filter thickness is facilitated by selecting such a material. FIGS. 3(a) to 3(c) show the relationship between the tube voltage (kV) and half-value layer (mm) in a case of using copper (thicknesses 0.1 and 0.5 mm), aluminum (0.1 mm), etc. as the filter 50, for example. The half-value layer is the thickness of a material in a case where the amount of radiation is halved by absorption with a specific material being disposed in an X-ray flux, and is an index used to evaluate the X-ray energy characteristics. More specifically, in a case where the half-value layer is thick, the energy becomes high.

As described above, in the X-ray detection device 10, according to the configuration described above, the line sensor 21 for which the scintillator 24 for low energy is disposed can detect X-rays in a low energy range having transmitted through the test subject S among the X-rays having emitted from the X-ray irradiator 5, as they are (without intervention of the filter 50), and can generate low energy image data. Meanwhile, the line sensor 22 for which the scintillator 25 for high energy is disposed can detect X-rays in a high energy range having transmitted through the test subject S and having been attenuated by the filter 50 among the X-rays having emitted from the X-ray irradiator 5, and can generate high energy image data. Furthermore, the X-ray detection device 10 positions the filter 50 using the holder 40 disposed outside of the housing 30. Accordingly, without any change of the arrangement and the configuration of the detector 20 in the housing 30 and without the scintillators 24 and 25 being scratched during filter replacement, the type of the filter 50 can be easily changed. In the X-ray detection device 10 where the line sensors are disposed close to each other, the detection sensitivities can be easily changed.

Figure 4:
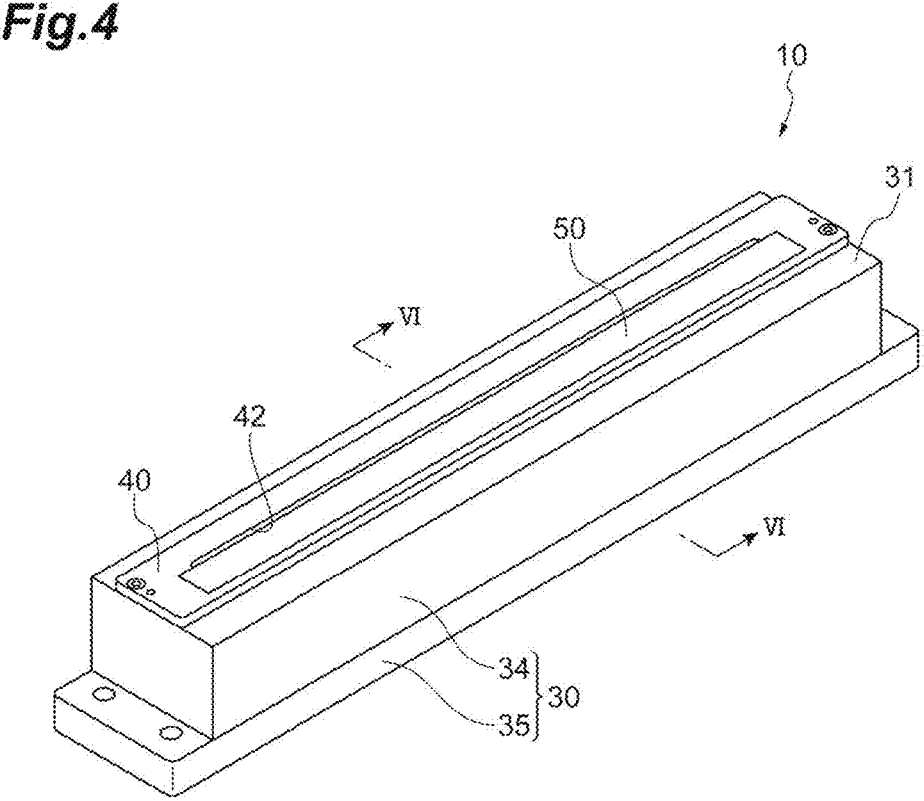
FIG. 4 is a perspective view showing an example of the X-ray detection device according to this embodiment.
Figure 5:
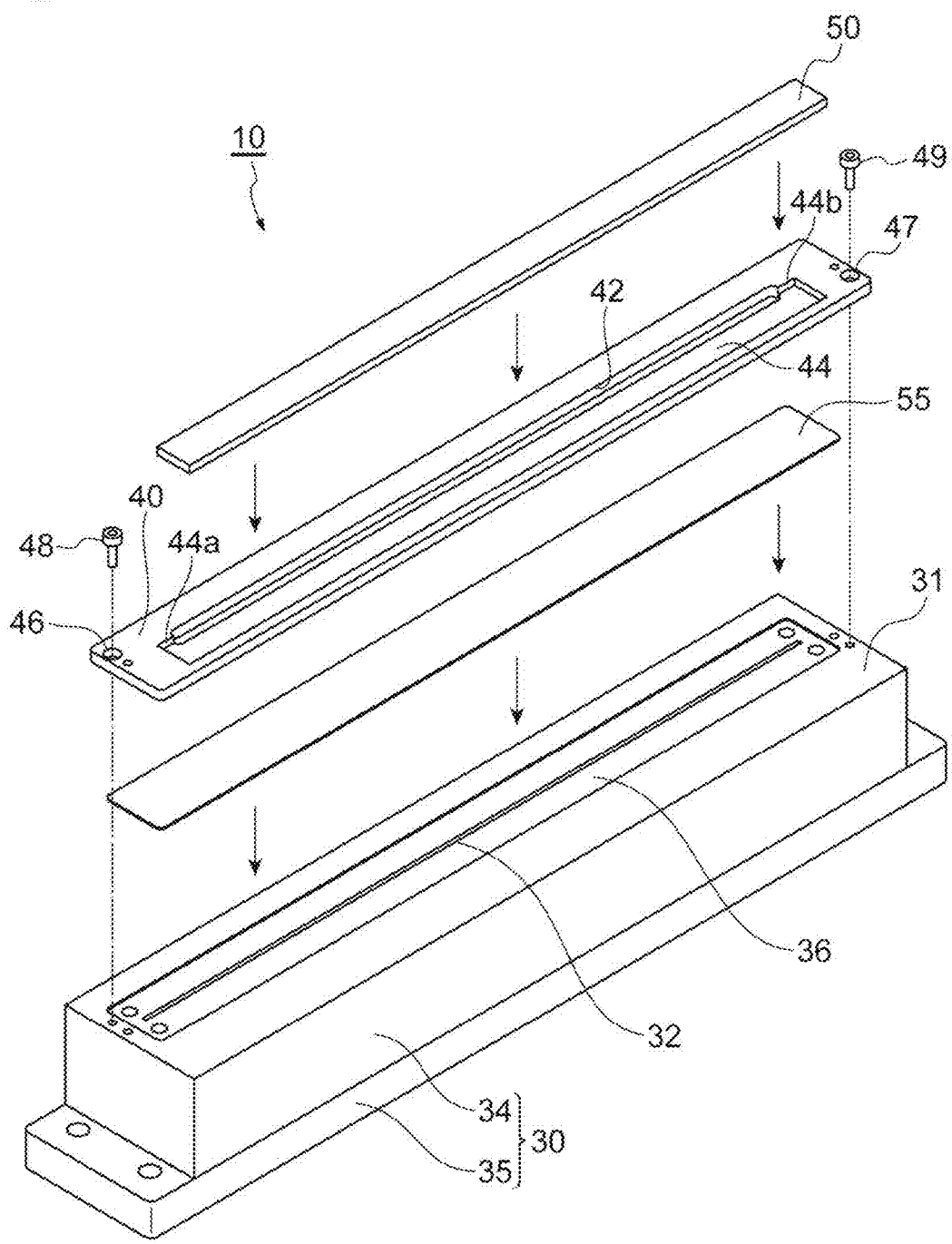
FIG. 5 is a partially exploded perspective view where an upper part of an example of the X-ray detection device shown in FIG. 4 is exploded.
Figure 6:
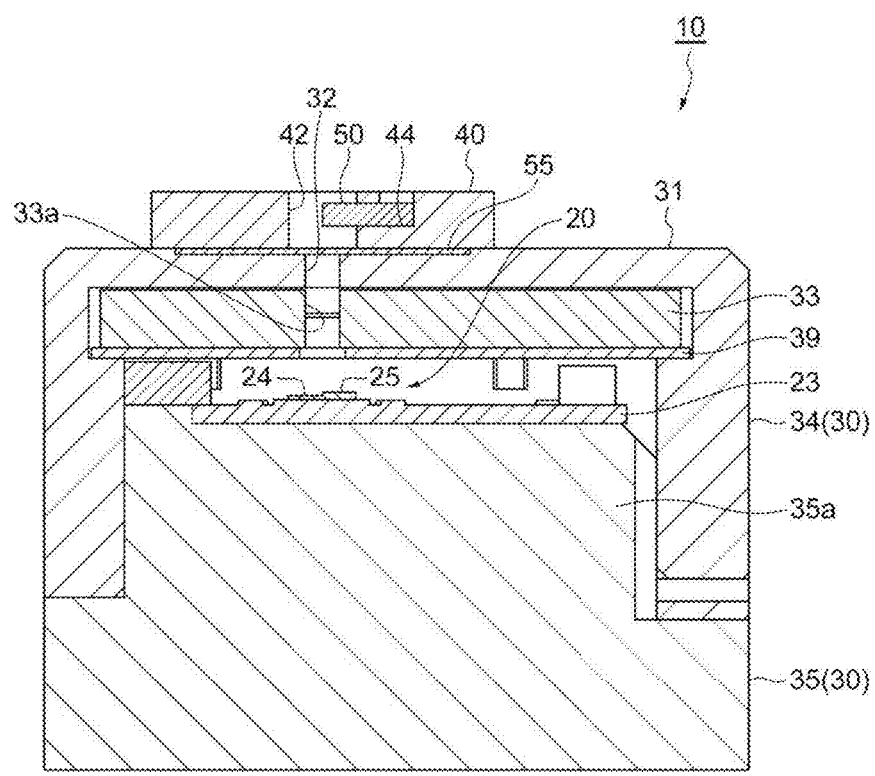
FIG. 6 is a sectional view taken along line VI-VI showing an example of the X-ray detection device shown in FIG. 4.
Figure 7:
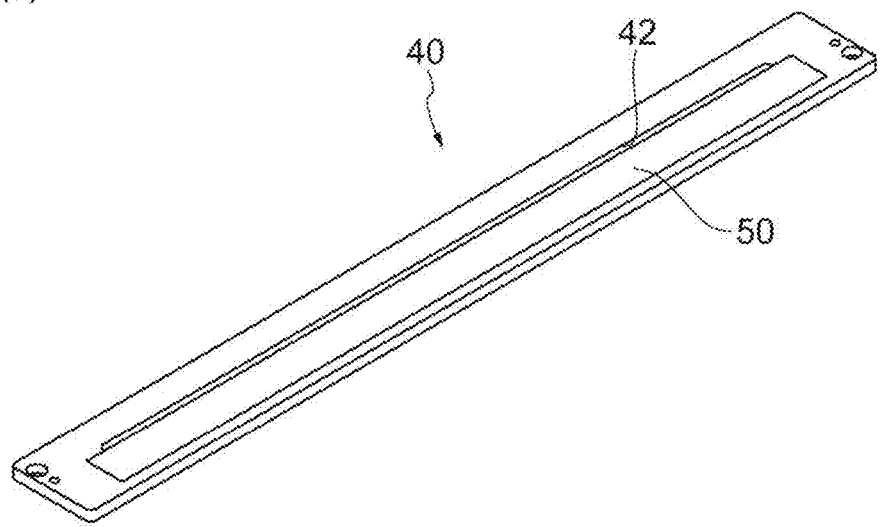
FIG. 7 is a perspective view showing a holder as an example in the X-ray detection device shown in FIG. 4, (a) shows a state where a filter is disposed in the holder, and (b) shows a state where the filter is not disposed in the holder.
Figure 7:
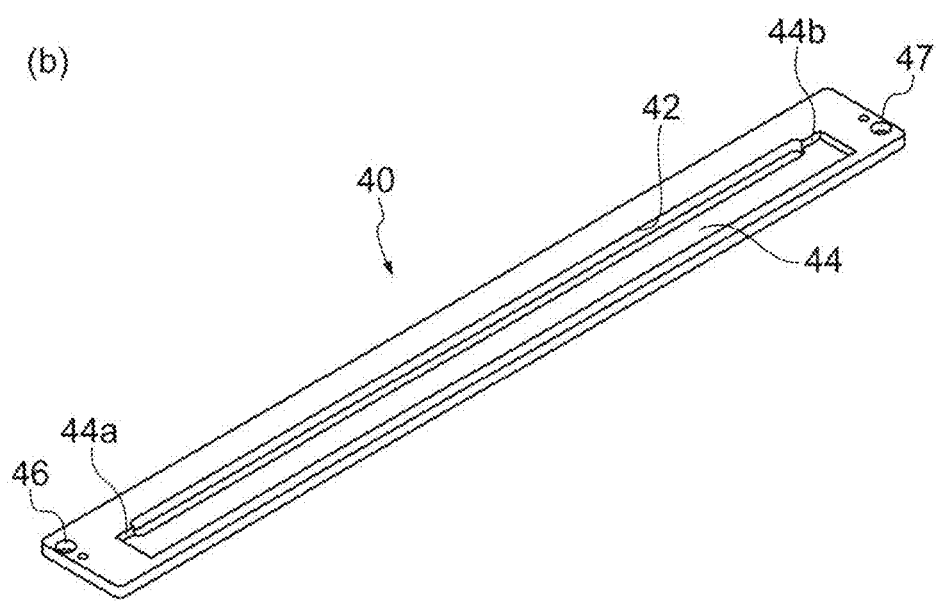

Subsequently, referring to FIGS. 4 to 7, an example of the X-ray detection device 10 is described. FIG. 4 is a perspective view showing an example of the X-ray detection device according to this embodiment. FIG. 5 is a partially exploded perspective view where an upper part of the example of the X-ray detection device shown in FIG. 4 is exploded. FIG. 6 is a sectional view taken along line VI-VI showing the example of the X-ray detection device shown in FIG. 4. FIG. 7 is a perspective view showing the holder and the filter as the example in the X-ray detection device shown in FIG. 4, (a) shows a state where the filter is disposed in the holder, and (b) shows a state where the filter is not disposed in the holder.

As described above, the X-ray detection device 10 includes the detector 20, the housing 30, the holder 40, and the filter 50. As shown in FIGS. 4 to 6, the housing 30 includes an upper housing 34 that has an internal space, and a lower housing 35 that is planar and includes a protrusion 35a at the center. The protrusion 35a of the lower housing 35 is fitted into the inside of the upper housing 34, thereby allowing the upper housing 34 and the lower housing 35 to be fitted with each other in order to prevent particles and the like from entering the inside of the housing 30. The upper housing 34 and the lower housing 35 are, for example, made of aluminum or the like. The substrate 23 of the detector 20 is disposed on the upper surface of the protrusion 35a of the lower housing 35, and the line sensors 21 and 22 (see FIG. 2) are formed on the substrate 23. The scintillator 24 is disposed on the line sensor 21. The scintillator 25 is disposed on the line sensor 22.

In the housing 30, a planar shield member 33 for preventing X-rays emitted from the X-ray irradiator 5 from entering the inside as they are is provided above the detector 20. The shield member 33 is provided with a slit 33a at the center. The slit 33a has a length and width corresponding to the other slits 32 and 42, and is formed so that the X-rays emitted from the X-ray irradiator 5 can reach the detector 20. A support plate 39 for supporting the shield member 33 is disposed under the shield member 33. The support plate 39 is attached to a dent on the inner surface of the upper housing 34 of the housing 30. The support plate 39 is made of stainless steel or the like, for example. A slit analogous to the slit 33a is provided also for the support plate 39.

As shown in FIGS. 5 to 7, the holder 40 is fixed onto the principal surface 31 of the housing 30 with fixing screws 48 and 49 through respective screw holes 46 and 47. The holder 40 has the slit 42 that is a through hole extending in the longitudinal direction at the center. The holder 40 includes a mount 44 that extends slightly longer in the longitudinal direction than the slit 42. The mount 44 is a non-penetrating depression, is formed to coincide substantially with the external shape of the filter 50, and is a part on which the filter 50 is to be mounted. Positioning sections 44a and 44b for preventing the filter 50 from moving are formed at the opposite ends of the mount 44. Movement of the filter 50 on one side surface is regulated by these positioning sections 44a and 44b. The other side surface of the filter 50 coincides, over its entire surface, with the inner surface of the mount 44 away from the slit 42. Movement on the opposite side is also regulated. The lower surface of the mount 44 does not completely coincide with the shape of the filter 50. A part of the filter 50 overlaps with the slit 42.

The filter 50 is mounted on the mount 44 of the holder 40 described above. The movement toward the slit 42 is regulated by the positioning sections 44a and 44b. Accordingly, the filter 50 is accurately positioned in such a way as to cover only a substantially half of the slit 42 of the holder 40. That is, the remaining half of the slit 42 is not covered with the filter 50. According to such a configuration, the X-rays having transmitted through the test subject S are divided into transmitted X-rays that are attenuated by the filter 50 and X-rays that are not attenuated by the filter 50, and the transmitted X-rays having not been attenuated enter the scintillator 24 for low energy, and the transmitted X-rays having been attenuated enter the scintillator 25 for high energy. The holder 40 is fixed onto the principal surface 31 of the housing 30 with the fixing screws 48 and 49 being respectively inserted into and fixed to the screw hole 46 formed near one corner and the screw hole 47 formed near the other corner disposed on the diagonal line. The light shield film 55 is inserted between the upper housing 34 and the holder 40. Entrance of unnecessary light is prevented by this light shield film. The light shield film 55 is mounted on a mount 36 in such a way as to cover the slit 32, thereby preventing particles and the like from entering the inside of the housing 30. The light shield film 55 is made of aluminum tape, polyethylene tape or the like, for example.

Here, a method of adjusting the X-ray detection device 10 described above is briefly described. As described above, in the X-ray detection device 10, the filter 50 is automatically positioned to be positioned only above the line sensor 22 of the detector 20 in the event that the filter 50 is mounted on the mount 44 of the holder 40. Accordingly, a plurality of filters 50 that have the same shape but different attenuations (different in thickness and material) are prepared first. The plurality of filters 50 are sequentially mounted on the mount 44 of the holder 40, and held at a predetermined position by the positioning sections 44a and 44b, and transmitted X-rays in each of the cases are detected. According to the results of the detected X-rays, the optimal filter that can more correctly detect the test subject S to be inspected and foreign matters, that is, can obtain a desired energy difference and S/N ratio, is selected from among the filters 50. According to such a method, the filter suitable for detection of the specific test subject S can be easily selected and changed. Note that the filter selected as described above is held and fixed at a predetermined position of the holder 40 as it is and is used for the X-ray detection device 10, thereby allowing the X-ray detection device 10 having the optimal detection sensitivity to be easily manufactured.

As described above, the X-ray detection device 10 according to this embodiment includes, as the detector, the line sensors 21 and 22 disposed close to each other, and partially covers, with the filter 50, the slit 42 that the holder 40 has, and the holder 40 holds the filter 50 at the predetermined position so that the line sensor 21 can detect the transmitted X-rays having not been attenuated by the filter 50 and the line sensor 22 can detect the transmitted X-rays having been attenuated by the filter 50. As described above, the holder 40 capable of positioning the filter 50 is separately provided, which can easily change the type (thickness or material) of the filter 50 that attenuates the X-rays. As a result, according to this embodiment, in the X-ray detection device 10 where the line sensors 21 and 22 are disposed close to each other, the detection sensitivities can be easily changed to various energy bands.

Furthermore, in the X-ray detection device 10 according to this embodiment, the holder 40 includes the positioning sections 44a and 44b for positioning the filter 50 so that the slit 42 is partially covered with the filter 50. As the positioning sections 44a and 44b are provided, even with filter replacement, the replaced filter is securely positioned at the predetermined site, which can easily maintain the state where the line sensor 21 detects X-rays having not been attenuated by the filter 50 and the line sensor 22 detects X-rays having been attenuated by the filter 50. Furthermore, this embodiment adopts the configuration allowing the positioning sections 44a and 44b to fix the opposite ends of the filter 50 in the longitudinal direction. Such adoption of the configuration of fixation at the opposite ends can suppress adverse effects and the like of the positioning sections 44a and 44b on detection of radiation at a central region.

According to the X-ray detection device 10 in this embodiment, it is preferable that the distances between the filter 50 and the line sensors 21 and 22 range from 10 to 30 mm, inclusive. In this case, the adverse effects of the scattered radiation of emitted X-rays can be reduced, and the transmitted X-rays can be detected by each of the line sensors 21 and 22 at a high sensitivity.

In the X-ray detection device 10 according to this embodiment, the detector 20 further includes a scintillator 24 disposed above the line sensor 21, and a scintillator 25 disposed above the line sensor 22. According to such a configuration, for example, scintillators having different performances can be adopted as the scintillators 24 and 25, and the same sensors can be adopted as the line sensors 21 and 22.

In the X-ray detection device 10 according to this embodiment, the housing 30 has the slit 32 corresponding to the slit 42 of the holder 40. Accordingly, the transmitted X-rays to be detected by the line sensors 21 and 22 pass through the respective slits 32 and 42, and the adverse effects of the material of the housing on detection of the transmitted X-rays by the line sensors 21 and 22 can be reduced. Note that in this embodiment, the X-ray detection device 10 further includes the light shield film 55 that covers the slit 32, and the light shield film 55 is disposed between the holder 40 and the housing 30. Accordingly, unnecessary light entering the detector 20 can be reduced, and foreign matters (powder, dust, etc.) can be prevented from entering the inside of the housing 30.

Furthermore, the X-ray inspection system 1 according to this embodiment includes the X-ray irradiator 5 that irradiates the test subject S with X-rays, the X-ray detection device 10, and the belt conveyer 3 that conveys the test subject S in a direction intersecting with the radiation direction of X-rays by the X-ray irradiator 5. As with the X-ray detection device 10, the X-ray inspection system 1 can easily change the type of the filter 50 that attenuates X-rays. Consequently, the detection sensitivities in the X-ray detection device 10, where the line sensors 21 and 22 are disposed close to each other, can be easily changed to various energy bands, and various types of test subjects can be tested.

The method for adjusting the X-ray detection device 10 according this embodiment comprises preparing a plurality of filters having different attenuation functions, as the filter 50; sequentially holding the plurality of filters at the predetermined position of the holder 40, and detecting the X-rays for each filter; and selecting an optimal filter among the filters according to results of the detected X-rays. According to such an adjusting method, the optimal filter can be easily selected from among the filters having different attenuation functions. Consequently, the X-ray detection device 10 can be easily adjusted, and the detection sensitivity in the X-ray detection device 10 can be easily and flexibly changed to various energy bands. In the X-ray detection device 10 adjusted by the adjustment method, the X-ray detection device 10 may be manufactured by further comprising holding the optimal filter selected by the selecting at the predetermined position of the holder 40. Such a manufacturing method can easily manufacture the X-ray detection device that can easily change the detection sensitivity to various energy bands.

The preferred embodiments of the present invention have thus been described in detail. The present invention is not limited to the above embodiments. Various modifications can be made. For example, in the embodiments described above, the scintillator is used to convert the radiation into visible light or the like. Alternatively, without use of the scintillator, a direct conversion type radiation detector (e.g., silicon semiconductor, amorphous selenium (a-Se) semiconductor, cadmium telluride (CdTe) semiconductor, cadmium zinc telluride (CdZnTe) semiconductor, etc.) may be used as the line sensor. In this case, there is no need to provide the scintillator separately, thereby allowing the number of components to be reduced.

In the aforementioned embodiments, the example of the X-ray detection device 10 has been described. There is, however, no limitation thereto. Various modification can be made. For example, the X-ray detection device 10 shown in FIG. 6 has the configuration where the X-rays having transmitted through the test subject S are divided into transmitted X-rays that are attenuated by the filter 50 and X-rays that are not attenuated by the filter 50, and the transmitted X-rays having not been attenuated enter the scintillator 24 for low energy, and the transmitted X-rays having been attenuated enter the scintillator 25 for high energy. However, according to another example of the X-ray detection device, the holder 40 may hold the filter 50 at the predetermined position so that the transmitted X-rays having attenuated by the filter can enter both the scintillator 25 for high energy and the scintillator 24 for low energy.

Figure 8:
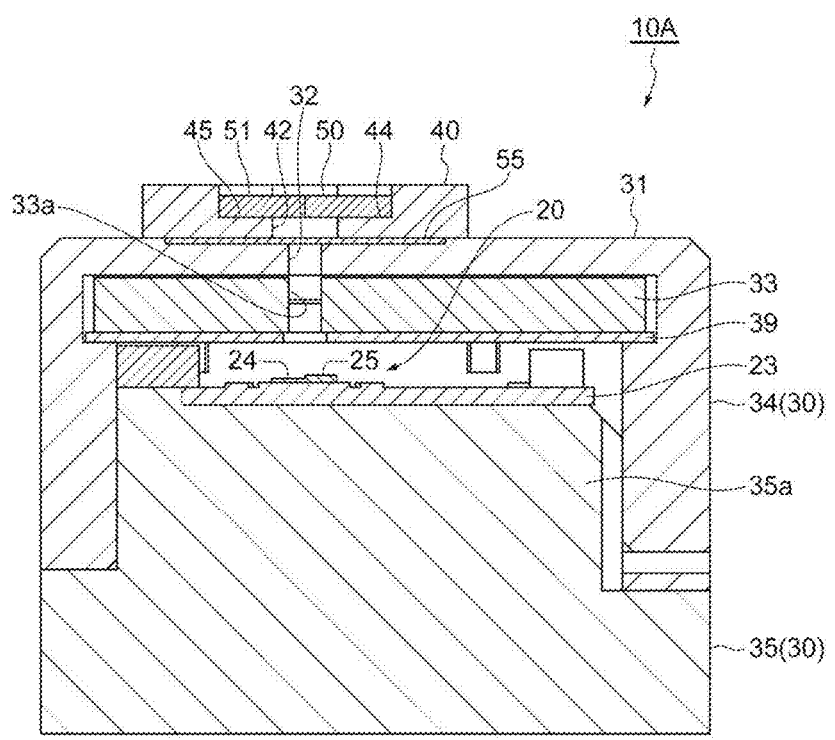
FIG. 8 is a perspective view showing another example of the X-ray detection device according to this embodiment.

For example, in an X-ray detection device 10A shown in FIG. 8, the holder 40 includes two mounts 44 and 45. A filter 50 is mounted on the mount 44 of the holder 40 while a filter 51 is mounted on the mount 45 of the holder 40. That is, the filter 50 and the filter 51 are held by the holder 40 in such a way as to cover the entire slit 42. According to such a configuration, the X-rays having transmitted through the test subject S are divided into transmitted X-rays that are attenuated by the filter 50 and X-rays that are attenuated by the filter 51, and the transmitted X-rays having been attenuated by the filter 51 enter the scintillator 24 for low energy, and the transmitted X-rays having been attenuated by the filter 50 enter the scintillator 25 for high energy. Note that the X-ray detection device 10A can be configured such that the filters 50 and 51 are positioned on the mounts 44 and 45 with reference to each other, and configuration elements, such as the positioning sections 44a and 44b, are not included.

The holder 40A, where the filters 50 and 51 can be mounted, is separately provided as described above. Consequently, in the X-ray detection device 10A according to the modification example, the energies of the transmitted X-rays entering the scintillator 24 for low energy and the scintillator 25 for high energy can be selectively changed by changing the types or thicknesses of the filters 50 and 51. That is, as with the X-ray detection device 10, the X-ray detection device 10A, where the line sensors 21 and 22 are disposed close to each other, allows the detection sensitivities to be easily changed to various energy bands. Note that in the X-ray detection device 10A, filters 50 and 51 may be an integrated filter member or separate filter members.

INDUSTRIAL APPLICABILITY

The present invention is applicable to a radiation detection device that detects radiation having transmitted through a test subject, a radiation inspection system, and a method for adjusting the radiation detection device.

REFERENCE SIGNS LIST

1 . . . X-ray inspection system (radiation inspection system), 3 . . . Belt conveyer (conveyer machine), 5 . . . X-ray irradiator (radiation source), 10, 10A . . . X-ray detection device (radiation detection device), 20 . . . Detector, 21, 22 . . . Line sensor, 24, 25 . . . Scintillator, 30 . . . Housing, 31 . . . Principal surface, 32 . . . Slit (second slit), 40 . . . Holder, 42 . . . Slit (first slit), 44a, 44b . . . Positioning section, 50 . . . Filter, 55 . . . Light shield film.

The invention claimed is:

1. A radiation detection device comprising:
a filter configured to attenuate a part of an incident radiation;
a detector configured to detect the radiation with a part thereof having been attenuated by the filter, wherein the detector comprises a first line sensor including first pixels having a first pixel width, the first pixels being one-dimensionally arranged, and a second line sensor including second pixels having a second pixel width, the second pixels being one-dimensionally arranged, the second line sensor being disposed in parallel to the first line sensor with an interval narrower than the first and second pixel widths;
a housing that places the detector therein; and
a holder disposed on an outer principal surface of the housing to hold the filter, the holder including a first slit allowing the incident radiation to pass,
wherein the holder holds the filter at a predetermined position so that the filter can cover at least a part of the first slit, and
wherein the second line sensor detects the radiation attenuated by the filter.

2. The radiation detection device according to claim 1, wherein the holder comprises a positioning section that positions the filter so that the first slit is partially covered with the filter.

3. The radiation detection device according to claim 2, wherein the positioning section fixes the filter at opposite ends in a longitudinal direction.

4. The radiation detection device according to claim 1, wherein a distance between the filter and the second line sensor ranges from 10 to 30 mm, inclusive.

5. The radiation detection device according to claim 1, wherein the detector further comprises a first scintillator disposed above the first line sensor, and a second scintillator disposed above the second line sensor.

6. The radiation detection device according to claim 1, wherein the first line sensor and the second line sensor are direct conversion type radiation detectors.

7. The radiation detection device claim 1, wherein the housing has a second slit corresponding to the first slit of the holder.

8. The radiation detection device according to claim 7, further comprising a light shield film covering the second slit, wherein the light shield film is disposed between the holder and the housing.

9. The radiation detection device according to claim 1, wherein the first line sensor detects the radiation having not been attenuated by the filter.

10. The radiation detection device according to claim 1, wherein the first line sensor detects the radiation having been attenuated by the filter.

11. A radiation inspection system, comprising:
a radiation source irradiating the test subject with radiation;
the radiation detection device according to claim 1; and
a conveyer machine that conveys the test subject in a direction intersecting with a radiation direction of the radiation by the radiation source.

12. The radiation detection device according to claim 1, wherein the filter is placed outside of the housing.

13. The radiation detection device according to claim 1, wherein the filter is apart from the detector.

14. A method for adjusting a radiation detection device, the radiation detection device comprising
a filter configured to attenuate a part of an incident radiation;
a detector configured to detect the radiation with a part thereof having been attenuated by the filter wherein the detector comprises a first line sensor including first pixels having first pixel width, the first pixels being one-dimensionally arranged and a second line sensor including second pixels having a second pixel width, the second pixels being one-dimensionally arranged, the second line sensor being disposed in parallel to the first line sensor with an interval narrower than the first and second pixel widths;
a housing that places the detector therein; and
a holder disposed on an outer principal surface of the housing to hold the filter, the holder including a first slit allowing the incident radiation to pass,
wherein the holder holds the filter at a predetermined position so that the filter can cover at least a part of the first slit, and
wherein the second line sensor detects the radiation attenuated by the filter,
the method comprising:
preparing a plurality of filters having different attenuation functions, as the filter;
sequentially holding the plurality of filters at the predetermined position of the holder, and detecting the radiation for each filter; and
selecting an optimal filter among the filters according to results of the detected radiation.

15. A method for manufacturing the radiation detection device adjusted by the adjustment method according to claim 14, further comprising
holding and fixing the optimal filter selected by the selecting at the predetermined position.

* * * * *